United States Patent [19]
Xie et al.

[11] Patent Number: 6,091,797
[45] Date of Patent: Jul. 18, 2000

[54] METHODS AND APPARATUS FOR GENERATING A SCOUT IMAGE

[75] Inventors: Min Xie, Waukesha; Jeffrey L. Agle, New Berlin, both of Wis.

[73] Assignee: General Electric Company, Milwaukee, Wis.

[21] Appl. No.: 09/140,291

[22] Filed: Aug. 25, 1998

[30] Foreign Application Priority Data

Oct. 29, 1997 [JP] Japan ................................. 9-296934
Nov. 18, 1997 [JP] Japan ................................. 9-317303

[51] Int. Cl.⁷ .................................................. G01N 23/04
[52] U.S. Cl. ............................................ 378/62; 378/901
[58] Field of Search ................... 378/4, 15, 62, 378/901

[56] References Cited

U.S. PATENT DOCUMENTS 5,613,492  3/1997  Feinberg ........................... 600/410

Primary Examiner—David V. Bruce
Attorney, Agent, or Firm—Armstrong, Teasdale; Christian G. Cabou; Phyllis Y. Price

[57] ABSTRACT

The present invention, in one form, is a system which, in one embodiment, improves the signal to noise of a scout image by aligning projection data in a z-axis. More specifically, by altering a table speed, a data acquisition system sampling rate, and a delay factor, the projection data collected from a detector array is aligned in the z-axis so that an improved scout image is generated. Particularly, and in one embodiment, the delay factor is adjusted so that the misalignment of the projection data collected from the detector is minimized.

24 Claims, 3 Drawing Sheets

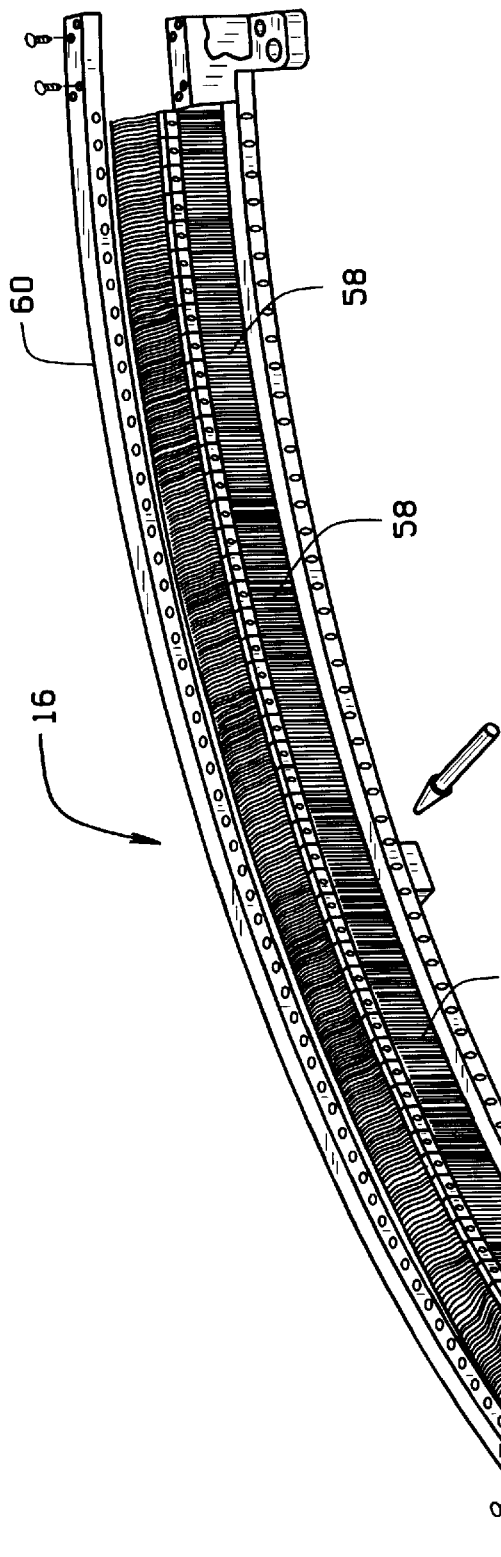
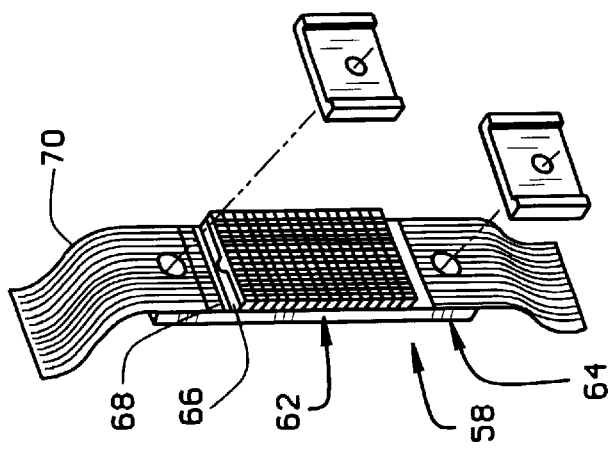

METHODS AND APPARATUS FOR GENERATING A SCOUT IMAGE

BACKGROUND OF THE INVENTION

This invention relates generally to computed tomography (CT) imaging and more particularly, generation of a scout image in an imaging system.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

In at least one known single slice CT system, a scout image is generated to identify significant boundaries in a patient or scanned object. The scout image is generated using a narrow slice thickness to improve the resolution of the image. As a result of the narrow slice thickness, however, the operator must trade-off signal noise and patient dose of x-ray exposure. If the operator selects too low of a dose, resulting higher data noise, the scout image is blurred. If the operator selects too high of a dose, the patient dosage is increased.

Accordingly, it would be desirable to provide a system for facilitating collection and alignment of multiple slices of projection data to generate an improved quality scout image. It would also be desirable to provide such a system without increasing the cost of the system.

BRIEF SUMMARY OF THE INVENTION

These and other objects may be attained in a system which, in embodiment, improves the signal to noise of an imaging system scout image by aligning projection data in a z-axis. More specifically, the imaging system includes a detector array having at least two rows of detectors in the z-axis, an x-ray source for radiating an x-ray beam toward the detector array, and a scaleable data acquisition system for converting the detector intensity signals to projection data.

In operation, by determining a table speed, a data acquisition system sampling rate, and a view delay factor, the projection data collected from a detector array is aligned in the z-axis so that an improved scout image is generated. Particularly, and in one embodiment, the delay factor is adjusted so that the misalignment of the projection data collected from the detector is minimized.

By aligning the projection data as described above signal to noise is improved resulting in an improved scout image. In addition, the improved scout image is generated without significantly adding to the cost of the system.

BRIEF DESCRIPTION OF THE DRAWINGS

FIG. 3 is a perspective view of a CT system detector array.

FIG. 4 is a perspective view of a detector module.

DETAILED DESCRIPTION OF THE INVENTION

Figure 1:
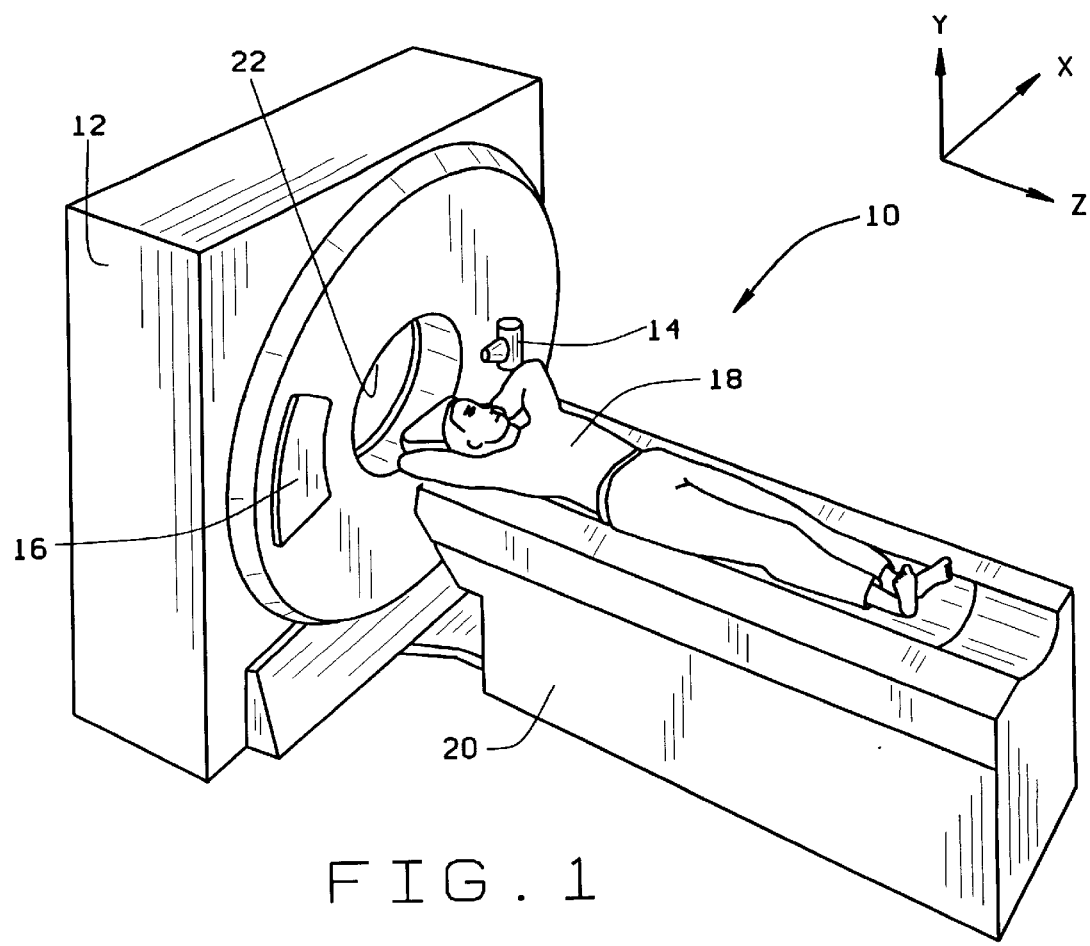
FIG. 1 is a pictorial view of a CT imaging system.

Referring to FIG. 1, a computed tomography (CT) imaging system 10 in accordance with one embodiment of the present invention is shown as including a gantry 12 representative of a "third generation" CT scanner. Gantry 12 has an x-ray source 14 that projects a beam of x-rays toward a detector array 16 on the opposite side of gantry 12. Detector array 16 is formed by a plurality of detector modules which together sense the projected x-rays that pass through a medical patient 18. Each detector module produces an electrical signal that represents the intensity of an impinging x-ray beam and hence the attenuation of the beam as it passes through patient 18.

During a scan to acquire x-ray projection data, gantry 12 and the components mounted thereon rotate about a center of rotation. A motorized table 20 positions patient 18 relative to gantry 12. Particularly, table 20 moves portions of patient 18 through a gantry opening 22 during a scan.

Figure 2:
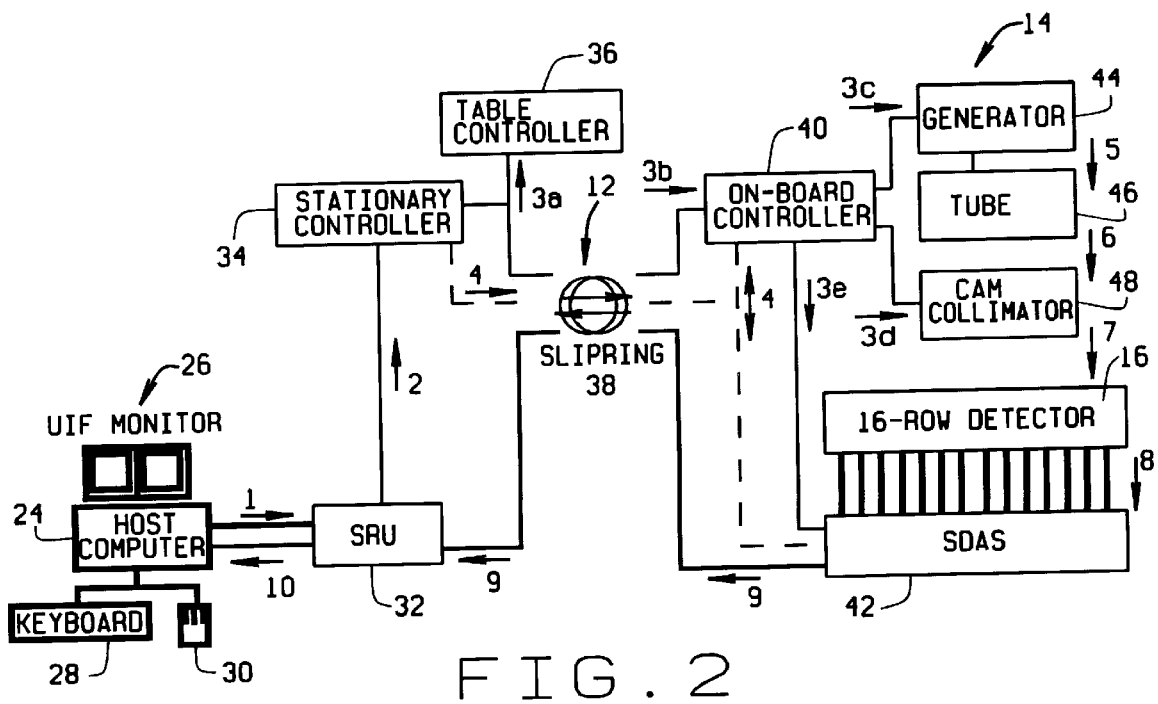
FIG. 2 is a block schematic diagram of the system illustrated in FIG. 1.

FIG. 2 is a block schematic diagram of the system illustrated in FIG. 1. As shown in FIG. 2, system 10 includes a host computer 24 coupled to a monitor (user interface) 26 for displaying images and messages to an operator. Computer 24 also is coupled to a keyboard 28 and a mouse 30 to enable the operator to input information and commands to computer 24. Computer 24 is coupled to a scan and reconstruction control unit (SRU) 32. SRU 32 also includes image generation controls. In one specific embodiment, SRU 32 includes a SGI PCI-based central processing unit which operates on an IRIX operating system. SRU 32 also includes an interface processor for interfacing with the data acquisition system (described below), and a scan data correction (SDC) digital signal processing board for performing preprocessing, which is known in the art. SRU 32 further includes an image generator for filtered backprojection and postprocessing operations, as is known in the art.

A stationary controller 34 is connected to SRU 32, and controller 34 is coupled to a table controller 36. Stationary controller 34 also is connected, through a slipring 38, to an on-board controller 40 and a scalable data acquisition system (SDAS) 42. Slipring 38 enables contactless transmission of signals across the slipring boundary and supports the necessary bandwidth for transmission of data and commands across the boundary. SDAS 42 samples and acquires the data from detector 16 and converts the sampled analog signals to digital signals. SDAS 42, in one specific embodiment, includes forty eight interchangeable converter cards to support four row data acquisition. For two row data acquisition, twenty four cards could be used. In one specific embodiment, there are sixty four input channels per converter card arid 1408 Hz sampling can be performed. SDAS 42 also includes a front-end pre-amplifier for amplifying the signals.

On-board controller 40 controls operation of x-ray source 14 and operation of SDAS 42. X-ray source 14 includes a high voltage generator 44 coupled to an x-ray tube 46. Tube 46 may, for example, be the tube known in the art as the Gemini-1 tube and currently utilized in at least some CT system commercially available from General Electric Company, Milwaukee, Wis., 53201. Beams projected by X-ray tube 46 pass through a prepatient cam collimator 48 and impinge upon detector 16 (illustrated as a 16 row detector). Cam collimator 48 also is controlled by on-board controller 40. Outputs from detector 16 are supplied to SDAS 42.

In FIG. 2, data flow is illustrated by bold lines, control flow is illustrated by normal lines, and real-time control flow is illustrated by dotted lines. The numeric identifiers associated with the flows are set forth below.

1: scan and reconstruction prescription from operator
2: scan prescription to "master" controller
3: scan parameters distributed
   3a: table position
   3b: rotating parameters
   3c: kV and mA selections
   3d: x-ray beam collimation and filter selections
   3e: detector slice thickness and SDAS gain selections
4: real-time control signals during scanning
5: high voltage
6: un-collimated x-ray beam
7: collimated x-ray beam
8: analog scan data
9: digital scan data
10: patient images Rotation of gantry 12 and the operation of x-ray source 14 are governed by controller 34. On-board controller 40, under the control of stationary controller 34, provides power and timing signals to x-ray source 14. SDAS 42 samples analog data from detector 16 and converts the data to digital signals for subsequent processing. SRU 32 receives sampled and digitized x-ray data from SDAS 42 and performs high speed image reconstruction. The reconstructed image is applied as an input to computer 24 which stores the image in a mass storage device.

Computer 24 also receives commands and scanning parameters from an operator via keyboard 28 and mouse 30. Monitor 26 allows the operator to observe the reconstructed image and other data from computer 24. The operator supplied commands and parameters are used by computer 24 to provide control signals and information. In addition, controller 36 controls motorized table 20 to position patient 18 (FIG. 1).

As shown in FIGS. 3 and 4, detector array 16 includes a plurality of detector modules 58. Each detector module 58 is secured to a detector housing 60. Each module 58 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 58 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, tn output, and a control line (not shown). Switch apparatus 66 is coupled between the photodiode array and SDAS 42. Particularly, each switch apparatus FET input is electrically connected to a photodiode array output and each switch apparatus FET output is electrically connected to SDAS 42, for example, using, flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 24. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to SDAS 42. In one embodiment defined as a 16 slice mode, decoder 68 enables switch apparatus 66 so that all rows of the photodiode array are electrically connected to SDAS 42, resulting in 16 separate, simultaneous slices of data being sent to SDAS 42. Cf course, many other slice combinations are possible.

In one specific embodiment, detector 16 includes fifty-seven detector modules 58. The semiconductor array and scintillator array 62 each have an array size of 16×16. As a result, detector 16 has 16 rows and 912 columns (16×57 modules), which enables 16 simultaneous slices of data to be collected with each rotation of gantry 12. Of course, the present invention is rot limited to any specific array size, and it is contemplated that the array can be larger or smaller depending upon the specific operator needs. Also, detector 16 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 5:
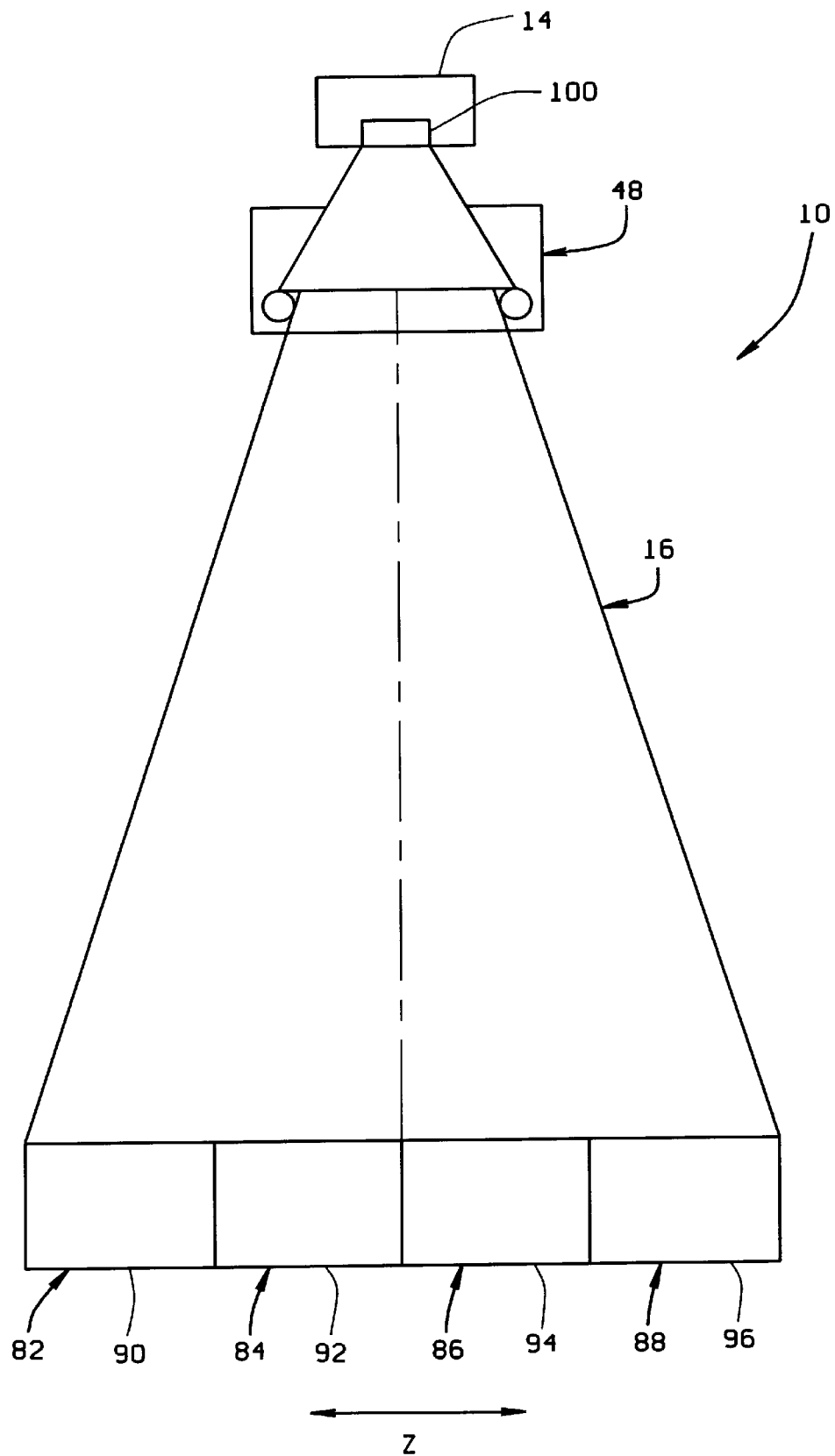
FIG. 5 is an z-axis schematic view of the CT imaging system shown in FIG. 5.

FIG. 5 is a schematic view of one embodiment of imaging system 10 in accordance with the present invention. In one embodiment, system 10 is a "four slice" system in that four rows 82, 84, 86 and 88 of detector cells are utilized to obtain projection data. Detector cells 90, 92, 94 and 96 are utilized for obtaining, or collecting projection data.

More specifically, and as shown in FIG. 5, x-ray beam 16 emanates from a focal spot 100 of x-ray source 14 (FIG. 2). X-ray beam 16 is collimated by pre-patient collimator 48, and collimated beam 16 is projected toward detector cells 90, 92, 94 and 96.

In one embodiment, a scout image is generated by applying a data alignment algorithm to the projection data collected by detector 16. The algorithm, in one embodiment, determines a plurality of parameters to improve the quality of the scout image. More specifically, utilizing the algorithm, operating parameters of system 10 are determined. Particularly, a sampling frequency for SDAS 42, a speed for table 20, a view compression factor, and a row delay factor. In one embodiment, the algorithm may be implemented in SRU 32. It will be apparent to those skilled in the art, of course, that such algorithm could be practiced in other components, for example, computer 24.

To produce a high quality scout image, the views from different rows of detector array 16 are aligned in the z direction by determining, or adjusting, the system operating parameters. The alignment compensates, or corrects, for the movement of table 20 so that the data collected from multiple rows of detector 16 over time may be combined to form a sharp scout image. In one embodiment, a view delay factor is applied to the projection data collected from rows 82, 84, 86 and 88 of detector array 16 to align the data. The collected data may be adjusted in either direction by the view delay Factor depending upon the direction of table 20. As a result of a cal-vectors being row dependent, the selection of the rows to be combined is applied after the air-cal correction where row dependent scan data correction is done.

To avoid distortion and produce a square pixel, the view data collected from SDAS 42 is compressed before preprocessing. A compression factor is applied to the view data to produce the square pixel. The compression factor is determined as follows:

$$N_c = \text{round}\left(\frac{SFOV \cdot F_{view}}{NUM_{pixel} \cdot V_{table}}\right) \quad (1a)$$

(in number of uncompressed views)

where:

$F_{VIEW}$=a number of views collected,
SFOV=a scan field of view,
$V_{table}$=a table speed, and
$NUM_{pixel}$=a number of pixels.

For example and in one embodiment, where SFOV=500 mm, $V_{table}$=100 mm/sec., and $NUM_{pixel}$=888, equation 1a is defined as:

$$Nc = \text{round}(5.631 \times 10^{-3} \cdot Fview) \quad (1b)$$

By applying the compression factor, a square pixel is generated. The square pixel allows identical vertical and horizontal interpolation coefficient tables, as known in the art, to be used. As a result, the scout image minifying, as known in the art, is simplified and generated faster.

In one embodiment, a sampling rate of SDAS 42 is determined, or adjusted, so that the number of views is adjusted. The adjusted sampling rate is selected to optimize the scout image quality and the amount of data required to be processed. As a result, the selection of the sampling rate must be considered along with the view delay factor.

In operation, the view delay factor is applied to the projection data collected from detector 16 so that the data collected from more than one detector row are aligned in the z direction for the same location of patient 18. More specifically, the delay factor, or time delay between rows, in number of uncompressed views is determined by:

$$D_{VIEW} = \text{round}\left(\frac{|Z_{1A} - Z_{1B}| ISO \cdot F_{VIEW}}{V_{TABLE}}\right) \quad (2a)$$

(in number of uncompressed views)

where:

$|Z1_A - Z1_B|$=distance between detector 1A and 1B at isocenter of detector 16.

For example, in one embodiment, where the slice thickness of detector array 16 is 1.25 mm so that $|Z1_A-Z1_B|$=1.25 mm and $V_{TABLE}$=100 mm/sec, $D_{VIEW}$ is:

$1.25 \cdot 10^{-3} \cdot F_{VIEW}$.

Utilizing equation 2a, the delay of a specific row may be determined by:

$$D_{ROW} = \text{row\_index} \cdot D_{VIEW}$$

where the first row or row__index =0 is the row of detector 16 that is the most advanced in the moving direction of table 20.

In an alternative embodiment, the view delay factor may be determined by comparing the difference images between the rows of detector 16. An optimal view delay factor is determined by identifying the view delay factor that generates the minimum difference or the finest outline of the scout image is the optimal view delay factor.

As a result of the round function in determining $D_{VIEW}$, an integer value is determined. However, the rounding operation introduces slight misalignment between combined views resulting in reduced image quality in the scout image. This mis-alignment is determined by:

$$\delta Z = \max\left(\left(\frac{|D_{VIEW} \cdot \text{row} - \text{round}(D_{VIEW} \cdot \text{row})| \cdot V_{TABLE}}{F_{VIEW}} \text{row} = 1, 2, 3\right) \text{(mm)}\right) \quad (3)$$

For example, where |Z1A−Z1B|=1.25 mm, $$\delta Z = \max\left(\frac{|1.25 \cdot 10^{-2} \cdot F_{VIEW} \cdot \text{row} - \text{round}(1.25 \cdot 10^{-2} \cdot F_{VIEW} \cdot \text{row})| \cdot V_{TABLE}}{F_{VIEW}} \text{row} = 1, 2, 3\right) \text{(mm)}.$$

The sampling frequency of SDAS 42 is determined so that a pixel aspect ratio is approximately equal to one. In one exemplary embodiment, as shown in Table 1, $\delta Z_D$ is the misalignment with the view delay factor equal to $D_{VIEW}$, and $\delta Z_{D-1}$ and $\delta Z_{D+1}$ are the misalignment with a view delay factor equal to $(D_{VIEW-1})$ and $(D_{VIEW+1})$, respectively. By determining the adjustable sampling rate of SDAS 42 and the view delay factor, the misalignment, $\delta Z$, may be optimized or reduced. For example, as shown in Table 2, the minimum misalignment is not inverse proportional to the sampling rate of SDAS 42. If the speed of table 20 is unchanged, the misalignment error may be reduced by altering the sampling rate of SDAS 42. As a result, the shape of the image pixel is slightly distorted as a result of the ratio of the speed of table 20 and the sampling rate of SDAS 42. For example, where FVIEW=550 views/sec., the misalignment error, $\delta Z$, is <0.068 mm and the pixel x/z ratio is 1.03, which represents a 3% distortion. In one embodiment of system 10, the x/y ratio may be similarly distorted, for example, x/y ratio=1.08, so that the error is evenly distributed between pixel x/z ratio distortion and misalignment.

In selecting the sampling rate of SDAS 42, the data transfer irate to SRU 32 is determined by:

$$T_{DATA} = F_{VIEW} \cdot \text{View\_width} \cdot \text{Size of (FFP)} \cdot Num_{ROWS} \text{ (bytes/sec)},$$

where:

Size of (FFP)=number of bytes of Funky Floating Point (FFP),

View_width=number of columns in detector array 16, and

Num_rows=number of rows used to collection data.

For example, in one embodiment, where FVIEW=179, Size of (FFP)=2, View_width=765, and Num_rows=2, $T_{DATA}$ is:

$$T_{DATA} = 179 \times 765 \times 2 \times 4 = 1070 \text{ KB/sec}.$$

As a result, slipring 38 must be capable of transmitting 1070 KB/second from SDAS 42 to SRU 32. In addition, a scout image data transfer rate, XFER, is determined as follows:

$$XFER = \frac{F_{VIEW} \cdot \text{image\_width} \cdot Sizeof(Int16)}{N_c} \text{ (bytes/second)},$$

where:

Sizeof(Int16)=2, and image_width=width of image after minifying.

For example, as further shown in Table 2, as the sampling rate of SDAS 42 is altered, the XFER rate is altered.

By determining the system parameters of SDAS sampling frequency, stable speed, view compression factor and the row delay factor, a high quality scout image is generated with minimum data transfer and processing load.

TABLE 1

| Nc | $F_{VIEW}$ (view/sec) | $D_{VIEW}$ (uncomp view) | $\delta Z$ (mm) | $\delta Z_{D-1}$ (mm) | $\delta Z_{D+1}$ (mm) |
|---|---|---|---|---|---|
| 1 | 179 | 2 | 0.265 | 0.6913 | 0.4260 |
| 2 | 358 | 4 | 0.133 | 0.4120 | 0.1467 |
| 3 | 537 | 7 | 0.074 | 0.1327 | 0.2400 |
| 4 | 716 | 9 | 0.021 | 0.1327 | 0.1466 |
| 5 | 895 | 11 | 0.048 | 0.1327 | 0.0908 |
| 6 | 1074 | 13 | 0.040 | 0.1327 | 0.0535 |
| 7 | 1253 | 16 | 0.027 | 0.0529 | 0.1067 |
| 8 | 1438 | 18 | 0.007 | 0.0628 | 0.0768 |

TABLE 2

| Nc | $F_{VIEW}$ (views/sec) | $T_{DATA}$ (KB/sec) | image XFER (KB/sec) | $\delta Z$ (mm) | x/z ratio |
|---|---|---|---|---|---|
| 1 | 179 | 1070 | 179 | 0.132 | 1.0 |
| 3 | 550 | 3288 | 187.7 | 0.023 | 1.03 |
| 4 | 716 | 4280 | 179 | 0.007 | 1.0 |
| 6 | 984 | 5880 | 179 | 0.03 | 1.08 |

The above described imaging system facilitates collection and alignment of projection data from a plurality of rows of a multislice detector array to generate an improved scout image. By collecting the data at different points in time and then aligning the projection data to the same anatomical point of the patient, the signal noise is cancelled, and the signal strength is increased. As a result, scout image quality is improved while using low x-ray source current. Further, the improved scout image is generated without significantly adding to the cost of the system.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, while the systems described herein have been two-slice and four-slice, any multi-slice system may be used. Accordingly, the spirit and scope of the invention are to be limited only by the terms of the appended claims.

What is claimed is:

1. A method of generating a scout image in an imaging system, the imaging system including a detector array and an x-ray source for radiating an x-ray beam toward the detector array, said method comprising the steps of:

scanning an object;

collecting projection data of the scanned object; and aligning the projection data in a z-axis.

2. A method in accordance with claim 1 wherein aligning the projection data comprises the step of applying a delay factor to the projection data.

3. A method in accordance with claim 2 wherein the detector array includes at least two rows of detector cells displaced along the z-axis, and wherein the delay factor is:

$$D_{VIEW} = \text{round}\left(\frac{|Z_{1A} - Z_{1B}|ISO \cdot F_{VIEW}}{V_{TABLE}}\right),$$

where:
$|Z_{1A}-Z_{1B}|ISO$=distance between a first detector, 1A, and a second detector row, 1B, at a detector isocenter,
$V_{TABLE}$=a table speed,
$F_{VIEW}$=a number of views collected, and
$D_{VIEW}$ is in number of uncompressed views.

4. A method in accordance with claim 3 wherein applying a delay factor to the projection data comprises the step of determining a delay factor for each row of the detector.

5. A method in accordance with claim 3 further comprising the step of determining a view misalignment.

6. A method in accordance with claim 4 wherein the view misalignment is:

$$\delta Z = \max\left\{\left(\frac{|D_{VIEW} \cdot \text{row} - \text{round}(D_{VIEW} \cdot \text{row})| \cdot V_{TABLE}}{F_{VIEW}} \text{row} = 1, 2, 3\right)\right\}.$$

7. A method in accordance with claim 1 wherein aligning the projection data in the z-axis comprises the step of applying a view compression to the projection data.

8. A method in accordance with claim 7 wherein the view compression is:

$$N_c = \text{round}\left(\frac{SFOV \cdot F_{VIEW}}{NUM_{pixel} \cdot V_{TABLE}}\right)$$

where:
$F_{VIEW}$=a number of views collected,
SFOV=a scan field of view,
$V_{TABLE}$=a table speed, and
$NUM_{pixel}$=a number of pixels.

9. A method in accordance with claim 1 wherein the imaging system further includes a scaleable data acquisition system, and wherein aligning the projection data in the z-axis comprises the step of determining a scaleable data acquisition system sampling rate.

10. A method in accordance with claim 9 further comprising the step of determining a data transfer rate.

11. A method in accordance with claim 10 wherein the data transfer rate is:

$$T_{DATA} = F_{VIEW} \cdot \text{View\_width} \cdot \text{Size of (FFP)} \cdot Num_{ROWS},$$

where:
Size of (FFP)=number of bytes of FFP,
View_width=number of columns in detector, and
$Num_{ROWS}$=number of rows used to collect projection data.

12. A method in accordance with claim 1 wherein the detector is a multislice detector.

13. A system for generating a scout image in an imaging system, the imaging system including a detector array and an x-ray source for radiating an x-ray beam toward the detector array, said system configured to:
scan an object;
collect projection data of the scanned object; and
align the projection data in a z-axis.

14. A system in accordance with claim 13 wherein to align said projection data, said system configured to apply a delay factor to said projection data.

15. A system in accordance with claim 14 wherein the detector array includes at least two rows of detector cells displaced along the z-axis, and wherein said delay factor is:

$$D_{VIEW} = \text{round}\left(\frac{|Z_{1A} - Z_{1B}|ISO \cdot F_{VIEW}}{V_{TABLE}}\right),$$

where:
$|Z_{1A}-Z_{1B}|ISO$=distance between a first detector, 1A, and a second detector row, 1B, at a detector isocenter,
$V_{TABLE}$=a table speed,
$F_{VIEW}$=a number of views collected, and
$D_{VIEW}$ is in number of uncompressed views.

16. A system in accordance with claim 15 wherein to apply a delay factor to the projection data, said system configured to determine a delay factor for each row of the detector.

17. A system in accordance with claim 15 further configured to determine a view misalignment.

18. A system in accordance with claim 18 wherein the view misalignment is:

$$\delta Z = \max\left\{\left(\frac{|D_{VIEW} \cdot \text{row} - \text{round}(D_{VIEW} \cdot \text{row})| \cdot V_{TABLE}}{F_{VIEW}} \text{row} = 1, 2, 3\right)\right\}.$$

19. A system in accordance with claim 13 wherein to align said projection data in the z-axis, said system configured to apply a view compression to said projection data.

20. A system in accordance with claim 19 wherein the view compression is:

$$N_c = \text{round}\left(\frac{SFOV \cdot F_{VIEW}}{NUM_{pixel} \cdot V_{TABLE}}\right)$$

where:
$F_{VIEW}$=a number of views collected,
SFOV=a scan field of view,
$V_{TABLE}$=a table speed, and
$NUM_{pixel}$=a number of pixels.

21. A system in accordance with claim 13 wherein the imaging system further includes a scaleable data acquisition system, and wherein to align said projection data in the z-axis, said system configured to determine a scaleable data acquisition system sampling rate.

22. A system in accordance with claim 21 wherein said system further configured to determine a data transfer rate.

23. A system in accordance with claim 22 wherein said data transfer rate is:

$$T_{DATA} = F_{VIEW} \cdot \text{View\_width} \cdot \text{Size of (FFP)} \cdot Num_{ROWS},$$

where:
Size of (FFP)=number of bytes of FFP,
View_width=number of columns in detector, and
$Num_{ROWS}$=number of rows used to collect projection data.

24. A system in accordance with claim 13 wherein the detector is a multislice detector.

* * * * *